United States Patent [19]

Huynh Dinh et al.

[11] Patent Number: 5,393,744
[45] Date of Patent: Feb. 28, 1995

[54] GLUCOSYL PHOSPHOTRIESTERS OF THYMIDINE

[75] Inventors: Tam Huynh Dinh, Croissy-sur-Seine; Catherine Gouyette, Vanves; Bernadette Dupraz, Maisons-Alfort; Jean Igolen, Le Mesnil-Saint-Denis; Nathalie Savatier, Creteil; Jean-François Nicolas, Noisy-le-Roi; Françoise Barre-Sinoussi, Issy-les-Moulineaux, all of France

[73] Assignee: Institut Pasteur, Paris, France

[21] Appl. No.: 460,959

[22] Filed: Jan. 29, 1990

[30] Foreign Application Priority Data

May 31, 1988 [FR] France .................. 88 07252

[51] Int. Cl.$^6$ .................... A61K 31/70; C07H 19/10
[52] U.S. Cl. ........................ 514/51; 514/23; 536/26.8; 536/28.2; 536/28.54; 536/117; 536/125
[58] Field of Search ............. 536/27, 28, 29, 17.1, 536/117, 27.22, 27.14, 26.8, 26.5, 28.2, 28.54, 124; 514/23, 51

[56] References Cited
U.S. PATENT DOCUMENTS 4,837,311 6/1989 Tam et al. .................. 536/27.14

OTHER PUBLICATIONS

Chemical Abstracts: vol. 90, No. 23, 182936y, Jun. 4, 1979.
Chemical Abstracts: vol. 98, No. 9, 72656q, Feb. 28, 1983.

*Primary Examiner*—John W. Rollins
*Assistant Examiner*—J. Oliver Wilson
*Attorney, Agent, or Firm*—Burns, Doane, Swecker & Mathis

[57] ABSTRACT

A compound having the following formula I:

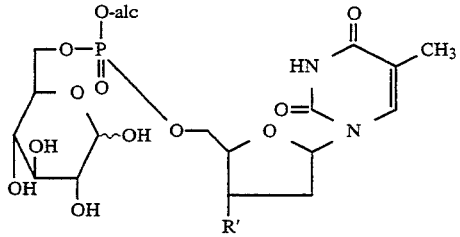

in which:
R' represents a hydrogen atom or an azido group,
alc represents an alkyl group of 1 to 4 carbon atoms, an alkoxy group of 1 to 4 carbon atoms or an amino group.

10 Claims, 10 Drawing Sheets

GLUCOSYL PHOSPHOTRIESTERS OF THYMIDINE

BACKGROUND OF THE INVENTION

1. Field of the Invention

The subject of the invention is glucosyl phosphotriesters of derivatives of thymidine having an activity against the retroviruses, in particular against HIV-1 and HIV-2.

2. Description of the Related Art

Numerous efforts have been devoted to the search for and the development of means for the detection of antibodies, of the prevention and treatment of this type of infection. For the prevention and treatment of the infections caused by HIV-1 and HIV-2 it has been suggested that the virus be placed in contact in vitro with derivatives of nucleosides.

In EP 0216510, is described the utilization of derivatives of purine bases, such as 2', 3'-dideoxyinosine (ddI), 2', 3'-dideoxyguanosine (ddG) or 2', 3'-dideoxyadenosine (ddA), and of the corresponding mono- and triphosphates.

Other antiviral nucleosides, constituted by derivatives of 3'-azido 3'-deoxythymidine (AZT) are described in EP 0196175.

SUMMARY OF THE INVENTION

The development by the inventors of a procedure for the synthesis of derivatives of phosphotriesters of nucleosides has made it possible to have available products, the study of which has revealed a favourable activity against the retroviruses.

Hence, the aim of the invention is to provide novel glucosyl phosphotriesters of derivatives of thymidine and a procedure for the synthesis of these derivatives.

In addition, the invention aims to provide compositions with an antiretroviral effect.

The derivatives according to the invention are characterized in that they correspond to the structure (I):

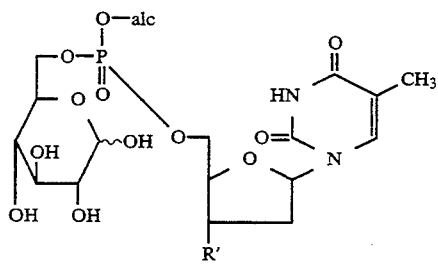

in which:
R' represents a hydrogen atom or an azido group,
-alc represents a saturated or unsaturated hydrocarbon radical of 5 to 30 carbon atoms, substituted if necessary.

The groups of substitution of the -alc radical advantageously represent an alkyl group of 1 to 4 carbon atoms, an alkoxy group of 1 to 4 carbon atoms, an amino group.

The phosphodiesters, precursors of the above glucosyl phosphotriesters, also enter into the scope of the invention.

The glucosyl phosphodiesters answer to the structure (II):

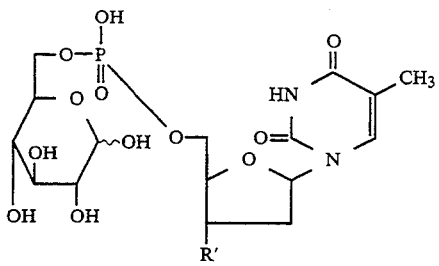

in which R' is such as defined above.

DETAILED DESCRIPTION OF THE PREFERRED EMBODIMENTS

Figure 1:
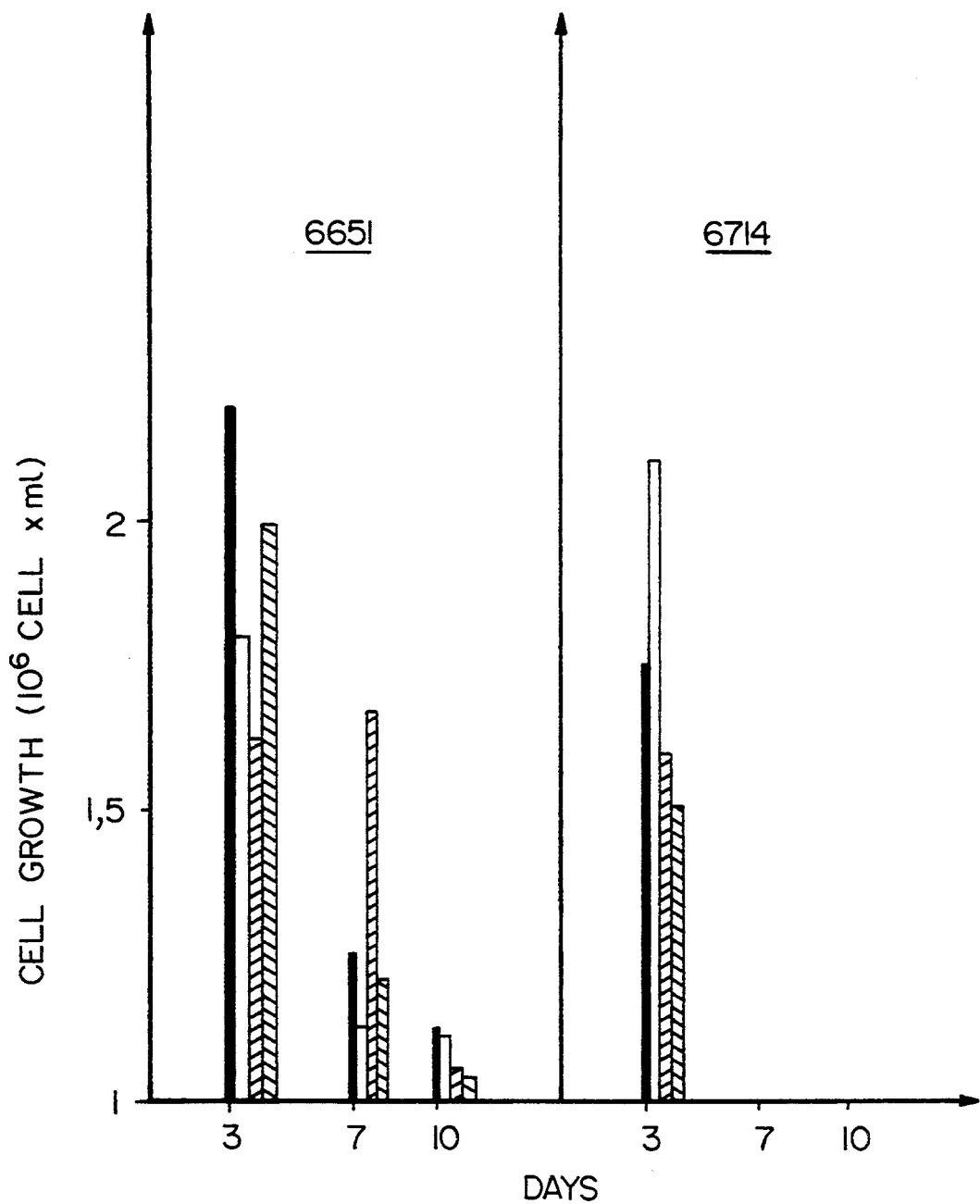
FIG. 1 shows cell growth as a function of time in the case of control cells and of cells treated with the derivatives according to the invention.

According to a variant of synthesis, these derivatives are obtained by implementing the following steps:

A derivative of glucose-6-phosphate of formula (III):

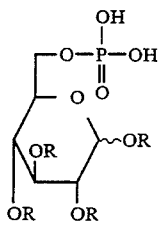

in which the radicals R, identical or different from each other, represent protecting groups of the hydroxyl function, this derivative being advantageously in the form of salt, is made to react with a derivative of thymidine of formula (IV):

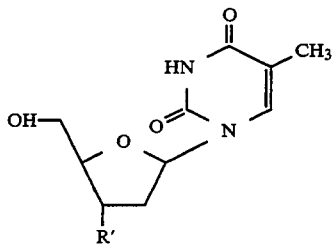

which leads to the phosphodiester of formula (V):

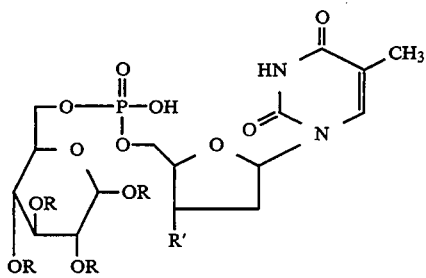

the protecting groups are removed and, in order to obtain the glucosyl phosphotriesters, the phosphodiester (V) is made to react with a reactive derivative containing the -alc group, which leads to the derivative of the phosphotriester of formula (VI):

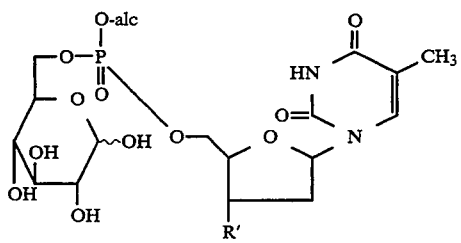

R' and alc representing in the above formulae the meanings given in relation to the structure of (I).

The steps which precede make it possible to obtain liposoluble derivatives of nucleotides capable of crossing a membrane, for example the envelope of a cell or the meningeal barrier, endowed with an anti-viral effect with regard to the retroviruses.

The coupling reaction between the derivatives (III) and (IV) is carried out at a temperature higher than room temperature, more particularly from 30° to 100° C. in an organic solvent.

Suitable solvents include pyridine, trichloroethane.

When pyridine is used as reaction solvent, the desired coupling is obtained by working at a temperature of 60° to 80° C., in particular close to 70° C. The reaction is carried out under an atmosphere of inert gas such as nitrogen or argon.

An excess of derivative (III) is advantageously used. An excess in moles of 1.5 to 2 makes it possible to carry out the coupling under satisfactory conditions.

In order to catalyst the reaction of formation of the phosphodiester, recourse is had to a compound such as TPSCl, DCCI (Warren C. D. and Jeanloz R. W. (1973), Biochemistry 12, 5038-5045 or Warren C. D. and Jeanloz R. W. (1972), Biochemistry 11 2565-2572) or trichloroacetonitrile (Cramer F. and Weimann G. (1961) Chem. Ber. 94 996-1007).

The derivative of formula (III) utilized in the coupling reaction is in the form of a salt, the reactivity of which favours the coupling.

It is a matter in particular of a pyridinium, morpholine, tetraethylammonium salt.

The protecting groups are removed prior to the attachment of an alkyl chain.

Among the groups suitable for the implementation of the invention, mention should be made of acyl groups, in particular acetyl, substituted alkyl such as benzyl, benzoyl.

The removal of these groups is carried out according to the standard techniques of organic chemistry, by working under conditions not effecting the structure of the phosphodiester (V) and its substituents.

The acyl groups of a mixture are removed for example with the aid of solutions of sodium hydroxide or of a $NH_3/CH_3OH$ mixture. The reactive derivative containing the alc group is advantageously a halide, in particular a bromide or iodide, or also a tosylate, or a sulfonium salt.

The reaction is carded out with advantage in an organic solvent, at a temperature higher than room temperature, in particular from 50° to 100° C.

Among the organic solvents which can be used, mention should be made of acetonitrile. The phosphodiester is preferably in the form of a salt of high reactivity and utilized in an excess of at least about 10 fold more, in moles, compared with the reactive derivative containing the alc group.

According to another variant of synthesis, a derivative of 6-glucose cyanoethylphosphate of formula (VII):

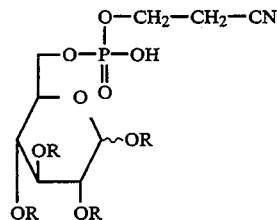

in which R is such as defined in respect to formula (III), this derivative being advantageously in the form of a salt, is made to react with a derivative of thymidine of formula (IV) above, then the blocking groups of the hydroxyl functions are removed.

The coupling reaction is advantageously carried out in an organic solvent at room temperature in the presence of TPSNT.

The derivative of formula (VII) is advantageously obtained by reaction of the corresponding derivative of glucose with cyanoethylphosphate in the form of a reactive salt.

The study of the derivatives of formulae (I) and (II) above has shown that at non-toxic doses for the human T lymphocytes, these derivatives are capable of inhibiting in vitro the cytopathogenic effect of the retroviruses.

These derivatives can hence advantageously be used to develop antiviral compositions. Such compositions are characterized in that they contain an efficacious amount of at least one derivative of formula (I) or (II) in combination with a pharmacological vehicle.

A process for treating in vitro human cells infected by retroviruses, particularly HIV-1 and HIV-2 is possible with the compositions of the present invention and in particular, with at least one derivative of formula (I) or (II).

Such compositions present themselves in forms suitable for administration by the oral, nasal, topical, rectal, vaginal, sub-cutaneous, intravenous, intramuscular or intradermal route.

The compositions which can be administered by the oral route include lozenges, tablets, granules, solutions or suspensions in aqueous or non-aqueous medium. Suppositories are utilized for administration by the rectal route and creams or foams by the vaginal route.

The formulations utilized for administration by the parenteral route are advantageously formed by sterile isotonic, aqueous or non-aqueous suspensions or solutions.

Other characteristics and advantages of the invention will become apparent by making reference to the examples which follow and to the figures.

EXAMPLE 1

Preparation of derivatives of 3'-azido thymidine or AZT.

1. Preparation of the pyridinium salt of 1, 2, 3, 4-tetra-O-acetyl 6-D-glucose phosphate of formula:

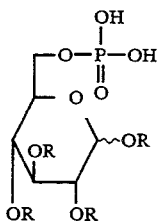

in which R = acetyl

The 1, 2, 3, 4-tetra-O-acetyl 6-D-glucose phosphate is prepared according to Whistler R. L., Doner L. W. and Kosik M. (1972) Methods in Carbohyd. Chem. Vol. VI, 711-712 Academic Press NY or Larry H. A. and Fischer H. O. L. (1946) J. Biol. Chem. 164 513-519.

5 g (16.44 mmoles) of the sodium salt of 6-D-glucose phosphate and 18 ml (190.4 mmoles) of distilled acetic anhydride in 20 ml of pyridine are subjected to stirring for 16 h at room temperature. An orangish solution is obtained with a white precipitate: the reaction is controlled by TLC (CH$_2$Cl$_2$/MeOH/H$_2$O: 60/35/5) starting Rf=0, acetylated product Rf: 0.61. The precipitate is filtered off and to the filtrate is cautiously added about 100 ml of ice and 10 ml of water in order to hydrolyse the anhydride in excess. The hydrolysis is allowed to continue for 30 minutes. The mixture is evaporated to dryness in a vacuum and then coevaporated several times with toluene. It is taken up in water and the aqueous phase is washed several times with dichloromethane. The aqueous phase is then reduced in volume before being passed onto a column of Dowex 50WX8 resin exchanged beforehand in the pyridinium form. The exit of the column is controlled by means of TLC and the good fractions are lyophilized m=6.54 g, yield=68%.

2. Preparation of 1, 2, 3, 4-tetra-O-acetyl 6-glucosyl 5'-(3'-azido) thymidinyl phosphate (Compound 1 in the formula below):

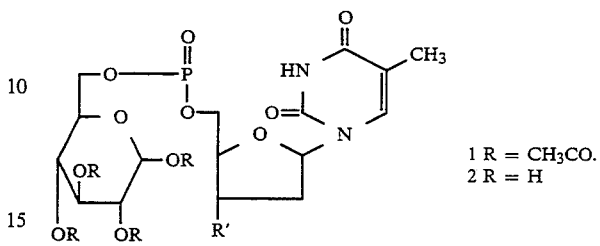

1 R = CH$_3$CO.
2 R = H 200 mg (0.75 mmoles) of 3'-azido thymidine (AZT) and 656 mg (0.75 mmoles × 1.5 excess) of 1, 2, 3, 4-tetra-O-acetyl 6-D-glucose phosphate in its pyridinium form are subjected to a co-evaporation three times with anhydrous pyridine. About 15 ml of anhydrous pyridine and 2.56 ml of trichloracetonitrile (0.75 mmoles × 35 excess) are added. The mixture is heated at 70° C. while stirring well and maintaining under an atmosphere of nitrogen for 16 h. It is evaporated to dryness in a vacuum, then the mixture is taken up in a minimum of dichloromethane and precipitated by petroleum ether. The petroleum either is decanted and the precipitate is chromatographed on a column of silica Merck 7734 R eluted with dichloromethane enriched in methanol. The compound is eluted at about a mixture with 10% methanol. m=540 mg yield: 95%, Rf=0.54 (CH$_2$Cl$_2$/MeOH/H$_2$O, 13/5/1).

3. Preparation of 6-glucosyl 5' (3'-azido)-thymidinyl phosphate (compound 2 in the above formula). This compound will be designated hereafter by the code 6715.

540 mg of product 1 previously obtained are used. The acetyl groups are removed in 1% sodium methylate in methanol for 10 minutes at room temperature. A slight cloudiness appears. It is verified by TLC that the reaction is complete. It is neutralized by the addition of Dowex 50Wx8 H+ R resin. At pH=7, the resin and the precipitate are filtered off and the methanolic phase is evaporated to dryness. It is taken up in a minimum of water and passed over a column of Biogel P2 200/400 mesh R eluted with water. The outflow from the column is detected by UV at 254 nm. After verification by means of TLC, the fractions containing the desired compound are lyophilized before being repassed over a column of silica C-18 eluted with water in order to complete the purification. m=283 mg, yield=67%, Rf=0.65, isopropanol/NH$_4$OH/H$_2$O, 7/1/2.

4. Preparation of the pyridinium salt of 1, 2, 3, 4-tetra-O-acetyl 6-D-glucose β-cyanoethyl phosphate.

The barium salt of the cyanoethyl phosphate is exchanged with a pyridinium salt by passing it over a column of Dowex H+ R and by collecting the product in pyridine.

The exchange involves 2.5 g of cyanoethyl phosphate. It is evaporated to dryness after passage over the column. 7.75 mM of pyridinium salt are obtained which are co-evaporated three times with pyridine. 2.58 mM of 1, 2, 3, 4-tetraacetyl glucose, i.e. 900 mg, are added. It is co-evaporated twice with pyridine. It is taken up in 20 ml of anhydrous pyridine, then 7 ml (58 mM) of freshly distilled trichloroacetonitrile are added. It is degassad with nitrogen and left at 75° C. under nitrogen for about 14 hours.

The solution is evaporated to dryness, taken up in a minimum of $CH_2Cl_2$ and precipitated with petroleum ether. The purification is carried out in a column of silica (9385 Merck R). It is eluted with $CH_2Cl_2$ enriched with MeOH. 760 mg of product (61%) are obtained. Rf: 0.51; $CH_2Cl_2$/MeOH (8/1).

5. Preparation of 6-glucosyl 5'-(3'-azido) thymidinyl phosphate 2 (6715) starting from 6-glucosyl cyano-ethyl phosphate.

200 mg (0.75 moles) of AZT and 469 mg (0.97 mmoles) of 1, 2, 3, 4-tetra-acetyl-6-glucose cyanoethyl phosphate are co-evaporated three times with pyridine. 4 ml of anhydrous pyridine and 616 mg of TPSNT (2 eq.) are added. It is left for 3 h at room temperature. After washing with a saturated solution of $Na_2CO_3$, then $H_2O$, the organic phase is dried over $Na_2SO_4$ and evaporated to dryness. The purification is carded out: 1) on a column of silica Merck 9385 R, 2) on a column of Sephadex LH 20 R eluted with the mixture THF/MeOH 95/5. 312 mg (55%) of the phosphotriester are obtained, from which the acetyl groups are removed with 1% sodium methylate during 15 minutes at room temperature. The same treatment as previously, after neutralization with a Dowex R resin gives the compound 2 (165 mg) identical with that obtained under 3.

6. Exchange of the pyridinium salt for the tetrabutyl-ammonium salt.

A column of Dowex 50Wx8 R resin is prepared which has been equilibrated in the tetrabutyl-ammonium form by placing Dowex 50Wx8 H+R resin to exchange with stirring during two hours in concentrated tetrabutyl-ammonium hydroxide, then by washing it with water washings to neutral pH.

The 283 mg of 2 obtained previously are passed over this column. The fractions absorbing at 254 nm are collected and lyophilized. 308 mg, yield: 85%, Rf: unchanged, Mass FAB 508 (M+1), HPLC: 2 peaks 5.00 and 5.33 min.

7. Preparation of 6-glucosyl hexadecyl 5'-(3'-azido) thymidinyl phosphate 3 designated hereafter by the code 6651.

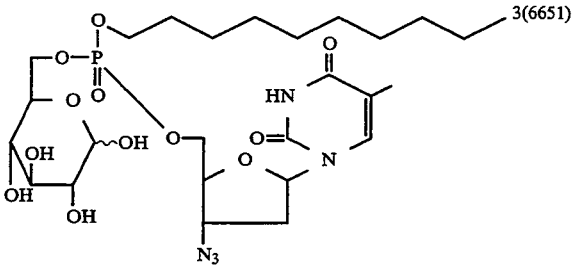

2.80 mg of the diester in the tetrabutylammonium form (0.372 mmoles) and 2.11 ml of 1-iodohexadecane (0.372 mmoles×18 excess) are evaporated in a vacuum with anhydrous acetonitrile. About 15 ml of anhydrous acetonitrile are then added and it is heated at 80° C. for 16 to 20 hours. The reaction is then checked by TLC. The mixture is evaporated to dryness, it is taken up in a minimum of dichloromethane and the solution is loaded onto a column of silica Merck 7734 R. The elution is performed with pure dichloromethane in order to remove the chain in excess. Subsequently, one enriches with methanol. The fractions containing the phosphotriester exit at a concentration of 10–15% of methanol. After concentration, these fractions are passed again over a column of Sephadex LH 20 R eluted with a THF/MeOH 80/20 mixture. 150 mg, 55%, are obtained, Rf=0.695, isopropanol/$NH_4OH$/$H_2O$ 7/1/2, Mass FAB+ 734 (M+1), HPLC retention time 13.77 min and 14.11.

EXAMPLE 2

Preparation of derivatives of derivatives of 3'-deoxy-thymidinyl.

The products, the synthesis of which is reported below, present the corresponding formulae given in example 1, the nucleotide being replaced by 3'-deoxy thymidinyl.

1. Preparation of 1, 2, 3, 4-tetra-O-acetyl 6-glucosyl 5'-(3'-deoxy) thymidinyl phosphate.

One operates as previously. 100 mg of 3'-deoxy-thymidine (ddT) (0.442 mmoles) and 388 mg of tetraacetyl 6-D-glucose phosphate (0.442 mmoles×1.5 excess) treated with 1.5 ml $CCl_3CN$, (0.442×34 excess) gave 2.5 mg, yield: 68%, Rf=0.6 ($CH_2Cl_2$/MeOH/$H_2O$ 13/5/1).

2. Preparation of 6-glucosyl 5'-(3'-deoxy)-thymidinyl phosphate (designated under the code 6714).

Operating as previously by purifying on Biogel R and silica C-18 R, the following results are obtained:

m=72 mg, yield=44%, Rf=0.58 (isopropanol/$N_{-}$$H_4OH$/$H_2O$ 7/1/2).

Exchange into $N(Bu)^+_4$ salt, m=90 mg, yield=96%, Rf unchanged, mass FAB=468 (M-1), HPLC retention time=10.77 min.

3. Preparation of 6-glucosyl hexadecyl 5'-(3'-deoxy) thymidinyl (designated under the code 6650).

On 137 mg of N(Bu+) diester (0.193 mmoles) and 1.091 ml of 1-iodo hexadecane (0.193 mmoles×18 excess), are obtained mm=28 mg, yield=21%, Rf=0.63 (isopropanol/$NH_4OH$/$H_2O$ 7/1/2). mass FAB+ =693 (M+1), HPLC retention time 3 peaks (12.71 min, 13.04 min, 13.38 min).

The measurements on HPLC reported in the examples are carried out by using reverse phase columns Nucleosil C18 R (¼°×15 cm) analytical, (½°×25 cm) preparative. The conditions are the following, A representing acetonitrile, and B $10^{-2}$ triethylammonium acetate, pH 7:

triester: 50% A 20 min, 95% A in A+B (in 20 min).
diester: 5% A 20 min, 25% A in A+B (in 20 min)

In vitro study of trans-membrane transport

The study of the behaviour of the phosphotriester of thymidine as model on unilamellar vesicles of 200 nm diameter in $^{31}P$ and $^{13}C$ NMR spectroscopy has shown that the phosphotriester crosses the lipid layer and is found intact in the interior of the vesicles, whereas the corresponding phosphodiesters either do not cross or cause the vesicles to rupture (detergent effect) at the concentrations used.

EXAMPLE 3

Study of the products with retroviral action.

The virus used is a recombinant retrovirus of murine origin (MoMLV) in which a reporter gene (LacZ) has been introduced. It is produced in transcomplementary lines which do not produce wild-type viruses.

Fixed amounts of LacZ recombinant retroviruses are placed in the presence of mouse infectable test cells (3T3) with or without the product to be tested. To each recombinant retrovirus corresponds a clone of β gal+ cells. The number of clones of βgal+ cells is read 48 hours after the infection. The % of the residual virus (not inhibited by the product) is indicated in the following table (mean of several independent experiments):

TABLE 2

|       | $10^{-4}$ M | $10^{-5}$ M | $10^{-6}$ M | $10^{-7}$ M |
|-------|------|------|------|------|
| AZT   | 0%   | 0%   | 0%   | 1%   |
| 6715  | 0%   | 0%   | 3%   |      |
| 6651  | 11%  | 65%  | 94%  |      |
| ddt   |      | 78%  | 87%  | 101% |
| 6714  |      | 4%   | 12%  | 66%  |
| 6650  |      | 79%  | 78%  | 96%  |

The products AZT, 6714 are active by themselves.

EXAMPLE 4

Study of the effect of the derivatives of phosphodiesters and phosphodiesters on the infectious potency of the HIV-1 virus in vitro.

1) Materials

2) Products Tested

The results obtained with the products of the examples called 6651 and 6714 are reported below. Each product was dissolved in DMSO at a concentration of $10^{-3}$M (stock solution), then in the culture medium immediately before use. The solution thus obtained was sterilized by filtration on a 0.22μ Millipore, then successive dilutions were made in the culture medium.

b) Culture medium

The cultures of human T lymphocytes are maintained in the medium RPMI 1640 containing 10% fetal calf serum (Seromeal), 1% of glummine (Gibco), 1% of antibiotics (PSN, Gibco), 10% of interleukin II (Biotest), 2 μg/ml of polybrene (Sigma) and a 1/2500 dilution of α-human semm-interferon. This medium is called complete medium.

The line of MT4 cells is cultivated at a concentration of $3 \times 10^5$ cells/ml in a RPM1640 medium containing 10% of fetal calf serum, 1% of antibiotics and 1% of glummine.

c) Cells

The cytotoxicity of the products was studied on human T lymphocytes obtained from peripheral blood of a sero-negative donor. Prior to the treatment, these lymphocytes are stimulated by phytohemagglutinin p (pHAp) (Difco) for 3 days.

The effect of the products on the multiplication of the HIV-1 virus was studied on human T lymphocytes obtained from peripheral blood of a sero-negative donor. The lymphocytes were isolated by Ficoll gradient (Pharmacia) then stimulated for 3 days by the phytohemagglutinin p (pHAp) (Difco) before being used for the treatment and infection by the HIV-1 virus.

The action of the products on the cytopathogenic effect of the HIV-1 virus was studied with the aid of the line of MT4 cells. This line is a line of human T cells transformed by the HTLV-1 virus. These cells are particularly sensitive to the HIV-1 virus since 6 to 7 days after superinfection by tiny quantities of HIV-1 virus, they show a considerable cytopathogenic effect leading to the death of 10 to 80% of the cells. The cytopathogenic effect is directly correlated with the infection of the cells by the virus, with its intracellular replication and with the expression of the viral antigens by the cells. An inhibition of this effect thus corresponds to an inhibition of the multiplication of the HIV-1 virus.

d) Virus

It is a question of supernatants of lymphoblastoid T cells (CEM line) infected by the HIV-1 virus (LAV strain). The activity of the undiluted viral preparation used for the human lymphocytes was 20000 cpm/ml.

2) Methods a) Study of the cytotoxicity of the products for the T cells.

$10^6$ lymphocytes stimulated by pHAp were treated for 10 days by increasing doses of the product ($10^{-5}$M; $5 \times 10^{-6}$M; $10^{-6}$M). The product was added at each cell passage carried out every 3 or 4 days. At each passage, the cells were counted after staining with trypan blue then resuspended at $10^6$ cells per ml in the complete medium containing or not increasing doses of the product. This experiment was carried out in a plate with 24 wells (Munc).

b) Action of the products on the infective potency of the HIV-1 virus in the case of human T lymphocytes. Action of a treatment after viral absorption.

Human lymphocytes stimulated beforehand by means of pHAp were infected by the HIV-1 virus (reverse transcriptase activity: 5000 cmp/$10^6$ cells). After 1 hour of viral absorption at 37° C., the lymphocytes were resuspended at $10^6$ cells per ml in a culture medium containing or not increasing doses of each product ($10^{-5}$M; $5 \times 10^{-6}$M; $10^{-6}$M). Every 3 or 4 days (cell passages), the cells were centrifuged then resuspended at $10^6$ cells per ml in a culture medium containing the product. The viral production was monitored at each passage (and this for 13 days) by measuring the reverse transcriptase activity present in 1 ml of culture supernatant. The viral production by the treated cells could thus be compared to that observed for untreated control cultures.

c) Measurement of the reverse transcriptase activity

The production of the HIV-1 virus by human T cells treated or not by each product was regularly monitored by measuring the reverse transcriptase activity present in 1 ml of culture supernatant. This method is described by Rey et al. in B.B.R.C. (1984), 124, 121–133. 1 ml of supernatant is concentrated 100 times by ultracentrifugation, then the enzymatic activity of this sample is determined in 50 μl of a reaction mixture containing 50 mM Tris pH 7.9, 20 mM KCl, 5 mM MgCl$_2$, 1 mM dithiothrietol, 0.05 OD/ml Poly A, 0.05 OD/ml oligodt 12–18, 5 μCi$^3$HTTP and 0.1% Triton×100. After 1 hour of incubation of 37° C., the acid-insoluble products are precipitated by 20% trichloroacetic acid, filtered on 0.45μ Millipore, then the β radioactivity contained in these reaction products is measured with the aid of a Kontron scintillation counter.

d) Action of the products on the cytopathogenic effect of the HIV-1 virus in the case of the MT4 cells. Study of the treatment after viral absorption.

The MT4 cells were infected by 100 μl of HIV-1 virus for $3.10^5$ cells in a volume of 1 ml. After 30 minutes of viral absorption at 37° C., the cells were washed, then resuspended at a concentration of $3.10^5$ cells/ml in a medium containing each product at the following concentrations: $10^{-5}$M; $45 \times 10^{-6}$M and $10^{-6}$M.

At day +3, the cell suspensions were restored to $3.10^5$ cells/ml after dilution with fresh medium. The product was added at the corresponding doses.

At day +7, the cytopathogenic effect was evaluated with the microscope after staining with trypan blue.

II—Results

1) Study of the cytotoxicity of the products in the case of human T lymphocytes.

In FIG. 1 is reported the variation of cell growth ($\times 10^6$ cells/ml) as a function of time, in days. The symbols utilized have the following meanings ▬ control cells; cells treated with the products obtained in the invention at concentrations of $10^{-3}$M ▭, $5 \times 10^{-6}$M ▧ and $10^{-6}$M ▥.

As FIG. 1 shows, the treatment of 10 days by the product 6651 is without significant effect on the growth of T cells in vitro at the doses used. When the cells are treated by the product 6714 at the same doses for 3 days, no effect is observed on cell multiplication.

2) Effect of the products on the infectious potency of the HIV-1 virus in the case of human T lymphocytes.

Figure 2:
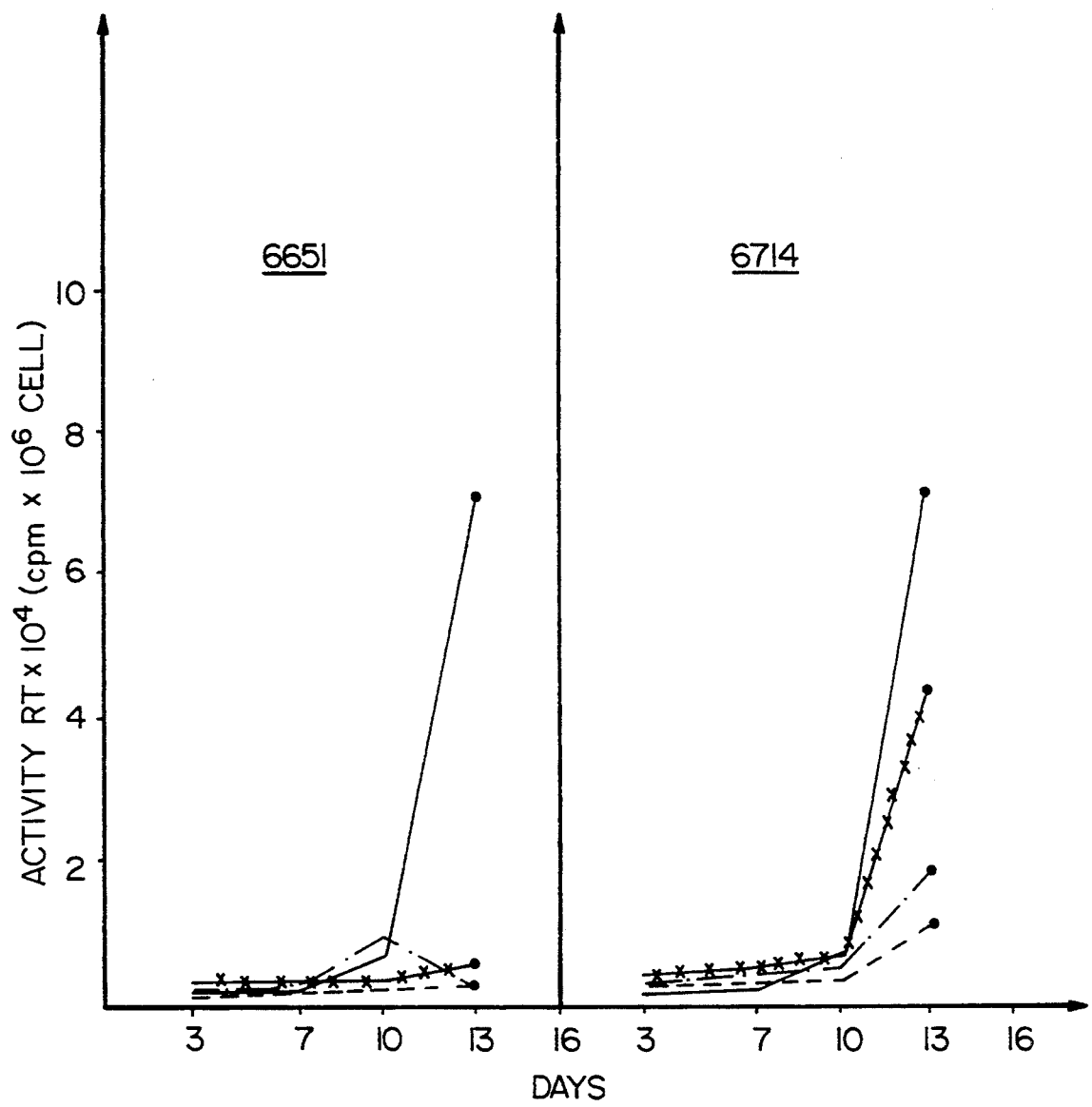
FIG. 2 shows the effect of the nucleotide derivatives on the infectious potency of HIV-1 for the human T lymphocytes.

FIG. 2 shows that the product 6651 at the dose of $10^{-5}$M leads to a total inhibition of the multiplication of the virus. A treatment by the product 6714 causes a partial inhibition proportional to the dose of the product used.

3) Action of the products on the cytopathogenic effect of the HIV-1 virus in the case of the MT4 cells.

The results obtained are reported in Table 1 below:

| | Cytopathogenic Effect at Day +7 | | |
|---|---|---|---|
| Product | Concentrations | Experiment No. 1 | Experiment No. 2 |
| 6651 | $10^{-5}$ M | − | − |
| | $5 \times 10^{-6}$ M | − | + |
| | $10^{-6}$ M | − | + |
| | $5 \times 10^{-7}$ M | + | + |
| 6714 | $10^{-5}$ M | NT | − |
| | $5 \times 10^{-6}$ M | NT | + |
| | $10^{-6}$ M | NT | + |
| — | 0 | + | + |

+ = 100% death of the cells at day +7
− = total inhibition of the cytopathogenic effect
NT = not tested The product 6651 inhibits this cytopathogenic effect at $10^{-6}$M in a first experiment and at $10^{-5}$M in a second experiment.

The product 6714 at $10^{-5}$ is shown to inhibit the cytopathogenic potency of the virus during an experiment.

On FIG. 2 is reported the activity $RT \times 10^4$ (cpm $\times 10^6$ cells) the function of time, in days. The curve "_" represents the results with the control virus; the results obtained by using the tested products at concentrations of $10^{-5}$M, $5 \times 10^{-6}$M and $10^{-6}$M, respectively, are represented by "---", "-.-" and "-x-x-x-".

EXAMPLE 5

Effect of the Drugs 6714 and ddT, and 6651 and AZT on the Replication of the HIV-1 Virus in the Macrophages of Sero-negative Donors

I) MATERIALS a) The products

The drugs 6651, AZT, 6714 and ddT were diluted in DMSO.

b) The virus HIV-1

The virus HIV-1 utilized is derived from a culture supernatant of CEM-LAV 1 cells; these latter are maintained by the addition at each passage (every 3 or 4 days) of uninfected CEM cells. The titre of the virus in the clarified culture supernatant is higher than $10^6$ cpm/ml in reverse transcriptase activity and $10^3$ infectious units/ml on lymphocytes of sero-negative donors.

c) The cells c.1 The lymphocytes

The lymphocytes were isolated from the peripheral blood of sero-negative donors on a Ficoll$^R$ gradient (MSL, Eurobio). The lymphocytes thus obtained were stimulated with the phytohemaglutinin p(PHA-p) for 3 days before their utilization.

The lymphocytes are cultivated in RPMI 1640 medium, supplemented with 10% of fetal calf serum, 10% of interleukin 2, 2 µg/ml of polybrene, 1% of glutamine, 1% of antibiotics.

c.1 The macrophages

The macrophages were obtained from a deleucocytation pocket. The mononucleated cells were separated on a Ficoll$^R$ gradient. The cells were adjusted to $50.10^6$ cells/ml in the RPMI 1640 medium (MBA) containing 20% fetal calf serum (Flow), 10 mM Hepes (Sigma), 1% of PSN and 1% of glutamine (Gibco). After 1 h of incubation at 4° C. with gentle shaking, the macrophages agglutinate among themselves. The agglutinated macrophages are sedimented for 15 mn at 4° C. The supernatant containing an enrichment in lymphocytes was removed and the pellet enriched in macrophages was diluted to $5.10^6$ cells/ml in the medium previously described. The cell suspension was then placed in Petri dishes of 60 mm diameter and placed at 37° C. for 1 h 30. The unattached cells are removed and the washed cell carpet was then detached with a scraper. The cells thus recovered were used directly for the study.

II) METHODS

For this study, the production of HIV-1 virus by infected macrophages in the presence or absence of the drugs 6714 or ddT and 6651 or AZT were monitored either in continuous culture for at least 30 days or after lysis of the macrophages at day +14 and infection of lymphocytes by this lysate.

1) Continuous culture

For each test, $15.10^6$ cells were or were not infected with the HIV-1 virus (6000 cpm/$10^6$ cells). After 1 h of absorption at 37° C., the cells were placed in 6-wells Costar plates and $5.10^{-5}$M or $10^{-5}$M of the drugs 6714 and ddT and $10^{-5}$M, $10^{-6}$M or $10^{-7}$M of the drugs 6651 and AZT were added to the culture medium. The medium was changed every 3 or 4 days and the reverse transcriptase activity was determined in the culture supernatant. The drugs were added at each passage to the culture medium at the respective concentrations indicated above.

2) Co-culture of the lysate of macrophages and lymphocytes

The quantity of cells placed in culture and the conditions of infection are identical with those previously described.

At day 14 after infection, the macrophages were lysed by two successive freezings to −20° C. and thawings at 37° C. The lysate recovered was then utilized as inoculum to infect $3.10^6$ activated lymphocytes derived from a sero-negative donor. After 1 h of absorption, the lymphocytes were adjusted to $10^6$ cells per ml and the drugs were added at the concentrations corresponding to those of the lysate.

The lymphocytes were subcultured every 3 or 4 days and an assay of the reverse transcriptase was carried out starting from the culture supernatant at each passage.

3) Measurement of the reverse transcriptase activity

The reverse transcriptase activity is assayed starting from 1 ml of culture supernatant concentrated 100 times by ultra-centrifugation for 5 mn at 95.000 rpm (Rotor TL 100$^R$ Beckman).

The pellet is resuspended in 10 μl of NTE Triton$^R$ × 100 0.1%. The enzymatic activity is revealed by the addition of 40 μl of the following reaction mixture: Tris 50 mM pH 7.9; KCl 20 mM; MgCl$_2$ 5 mM; dithiothreitol 1 mM: polyrA 0.05 O.D/ml; oligodT$^{12\text{-}18}$ 0.05 O.D./ml and $^3$HTTP 5 μCi.

After 1 h at 37° C., the acid-insoluble products are precipitated by 20% trichloroacetic acid, filtered onto 0.45μ Millipore$^R$ and the B radioactivity is measured with the aid of a Kontron scintillation counter.

III) RESULTS

1) Continuous culture of the macrophages

The FIGS. 3a, 3b, 3c, 3d show the vital production obtained with macrophages in continuous culture, infected or not, treated or not, respectively with the drug 6714, ddT, 6651 and AZT for 42 days, at different concentrations.

Figure 3A:
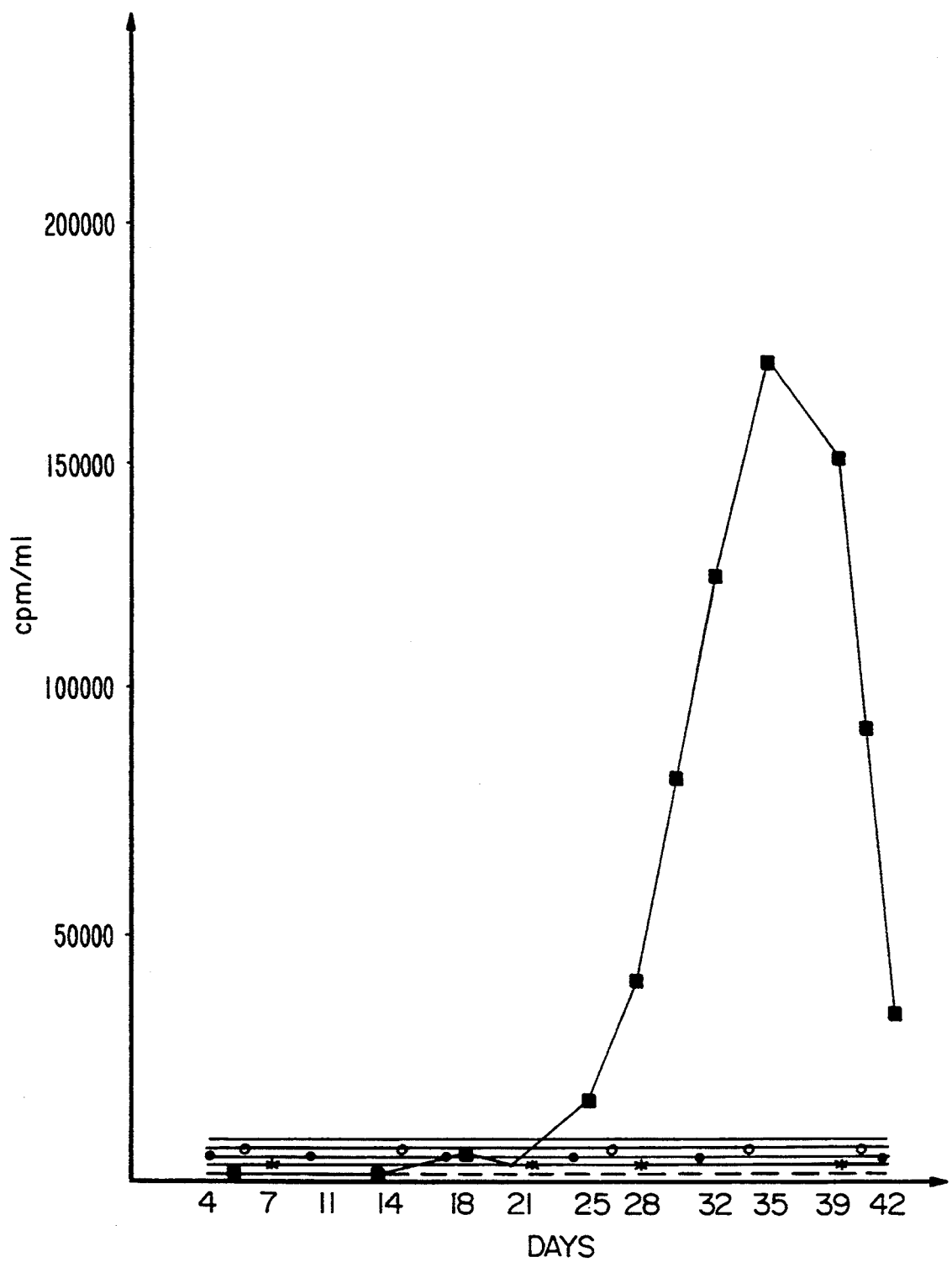
FIG. 3a shows the vital production obtained with macrophages in continuous culture, infected or uninfected, treated or not, with the drug 6714 for 42 days at different concentrations.
Figure 3B:
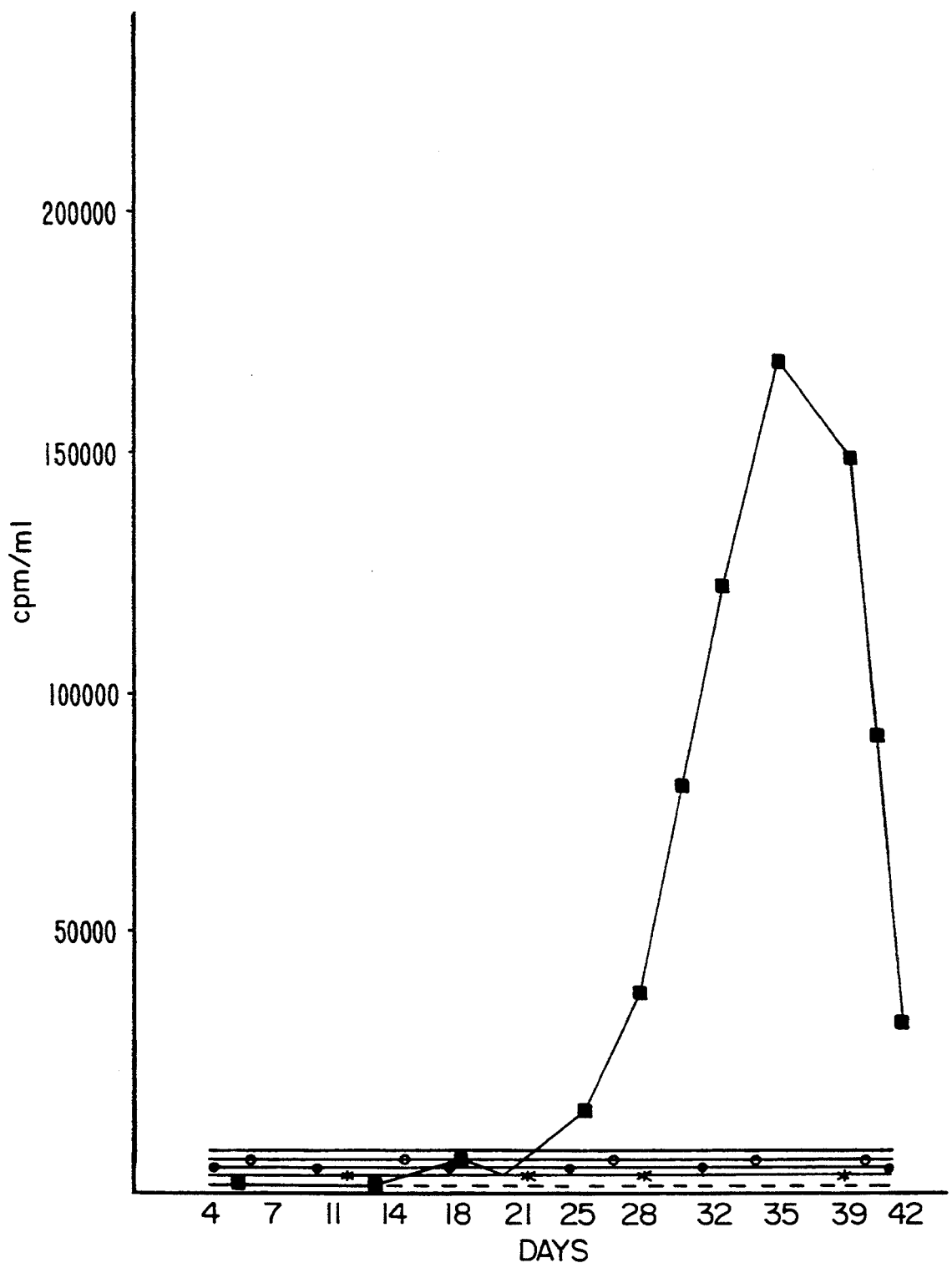
FIG. 3b shows the vital production obtained with macrophages in continuous culture, infected or not, treated or untreated, with the drug ddT for 42 days at different concentrations.

The symbols utilized in the figures are the following:
FIGS. 3a and 3b:
—⊖—⊖— infected macrophages treated with $5.10^{-5}$M of 6714 or ddT, respectively,
—✻—✻— infected macrophages treated with $10^{-5}$M of 6714 or ddT,
—■—■— infected macrophages untreated,
— — — uninfected macrophages treated with $5.10^{-5}$M of 6714 or ddT,
—●—●— uninfected macrophages treated with $10^{-5}$M of 6714 or ddT and
——— uninfected macrophages untreated.

Figure 3C:
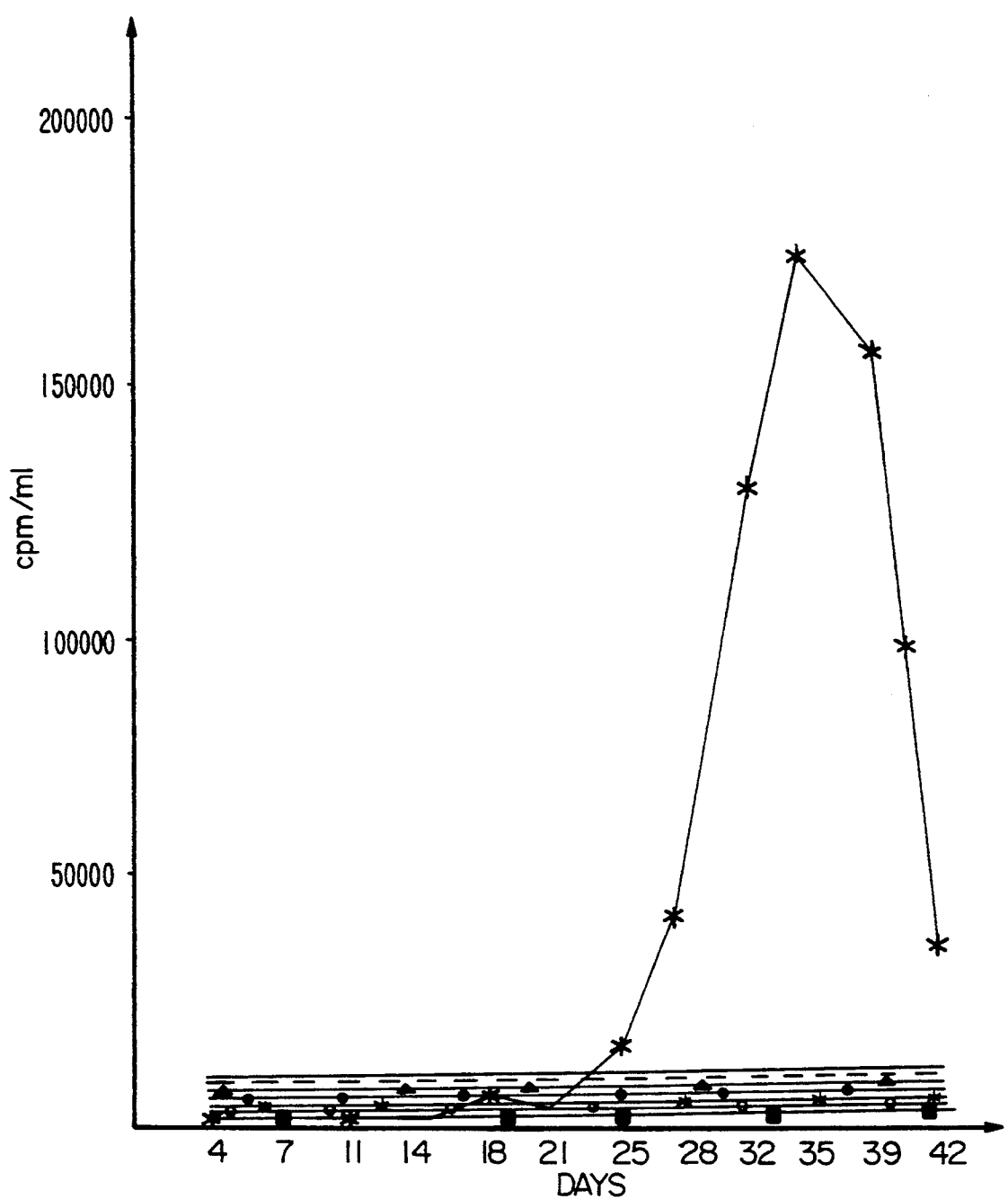
FIG. 3c shows the viral production obtained with macrophages in continuous culture, infected or not, treated or untreated, with the drug 6651 for 42 days at different concentrations.
Figure 3D:
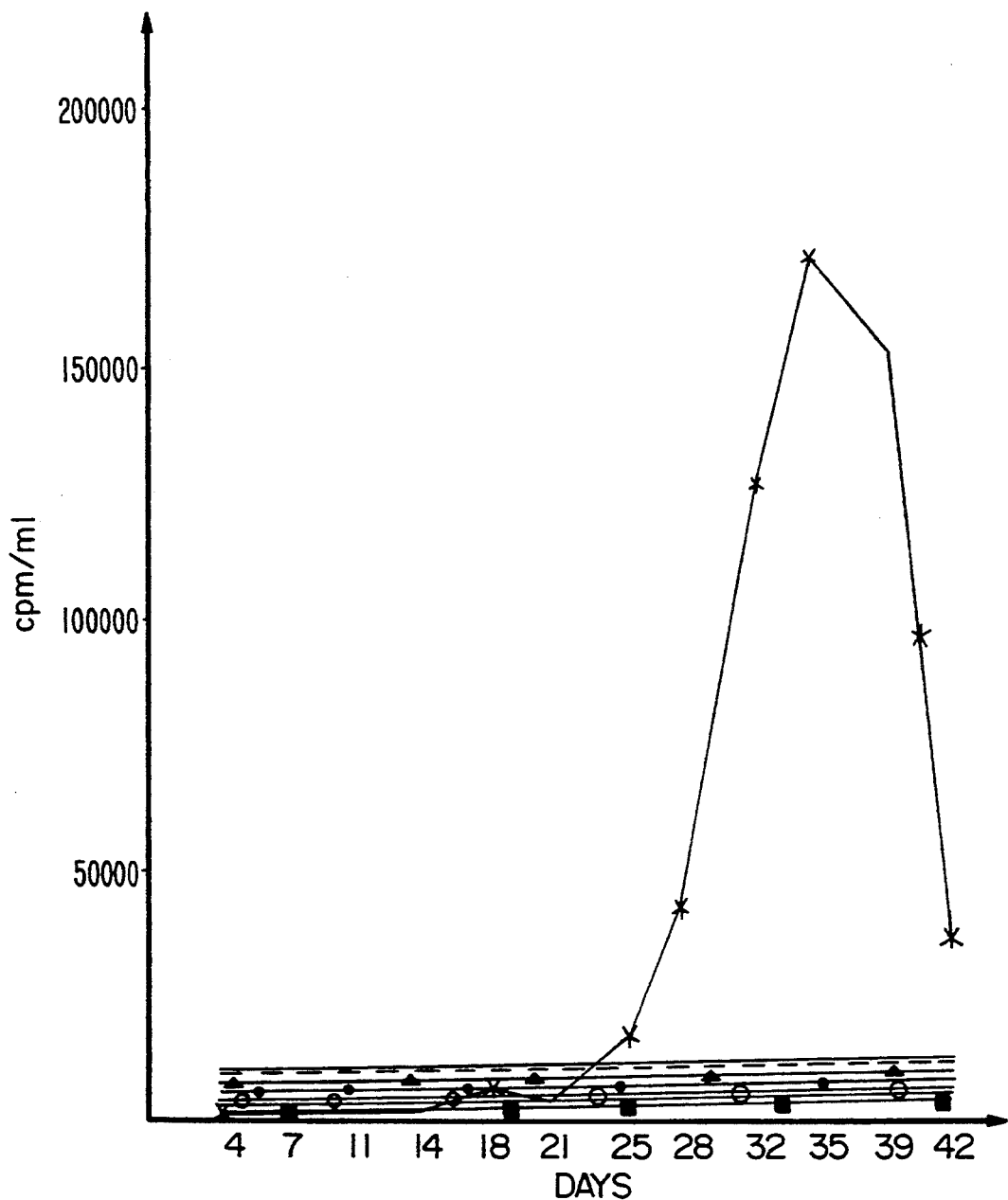
FIG. 3d shows the vital production obtained with macrophages in continuous culture, infected or not, treated or untreated, with the drug AZT for 42 days at different concentrations.

FIGS. 3c and 3d:
—⊖—⊖— infected macrophages treated with $10^{-5}$M of 6651 and AZT respectively,
—●—●— infected macrophages treated with $10^{-6}$M of 6651 and AZT,
—▲—▲— infected macrophages treated with $10^{-7}$M of 6651 and AZT,
—★—★— infected macrophages untreated,
— — — uninfected macrophages treated with $10^{-5}$M of 6651 and AZT,
—●—●— uninfected macrophages treated with $10^{-6}$M of 6651 and AZT,
—■—■— uninfected macrophages treated with $10^{-7}$M of 6651 and AZT, and
——— uninfected macrophages untreated.

No viral production is detected in the culture supernatant of infected and treated macrophages, whatever the drug added and concentration tested, unlike untreated infected macrophages in which a marked viral production is observed at day+35.

2) Infection of activated lymphocytes by the lysates of infected or uninfected macrophages, treated or not with the drugs 6714 or ddT and 6651 or AZT cultivated for 14 days.

The FIGS. 4a, 4b, 4c, 4d show the infective potency on activated lymphocytes of the lysates of infected or uninfected macrophages, treated or not, respectively with the drugs 6714, ddT, 6651 and AZT.

Figure 4A:
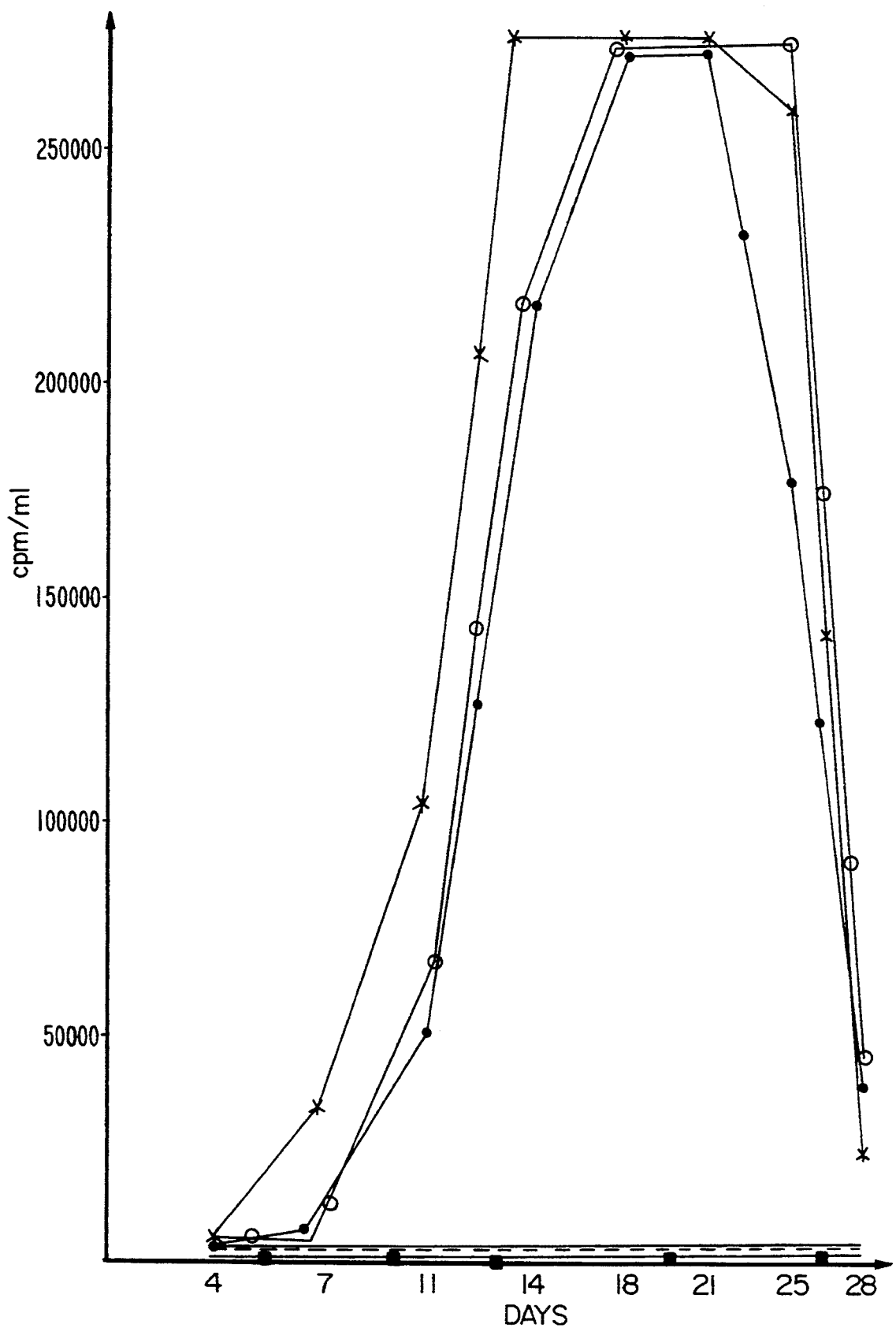
FIG. 4a shows the infective potency on activated lymphocytes of the lysates of infected or uninfected macrophages, treated or untreated, with the drug 6714.

The symbols utilized in the FIGS. 4a to 4d have the following meanings:
FIG. 4a:
—⊖—⊖— Lysate of infected macrophages treated with $5.10^{-5}$M of 6714+lymphocytes treated with $5.10^{-5}$M of 6714,
—●—●— Lysate of infected macrophages treated with $10^{-5}$M of 6714+lymphocytes treated with $10^{-5}$M of 6714,
—✻—✻— Lysate of infected macrophages untreated-+untreated lymphocytes,
— — — Lysate of uninfected macrophages treated with $5.10^{-5}$M of 6714+lymphocytes treated with $5.10^{-5}$M of 6714,
—□—□— Lysate of uninfected macrophages treated with $10^{-5}$ of 6714 +lymphocytes treated with $10^{-5}$M of 6714,
——— Lysate of uninfected macrophages untreated+untreated lymphocytes.

Figure 4B:
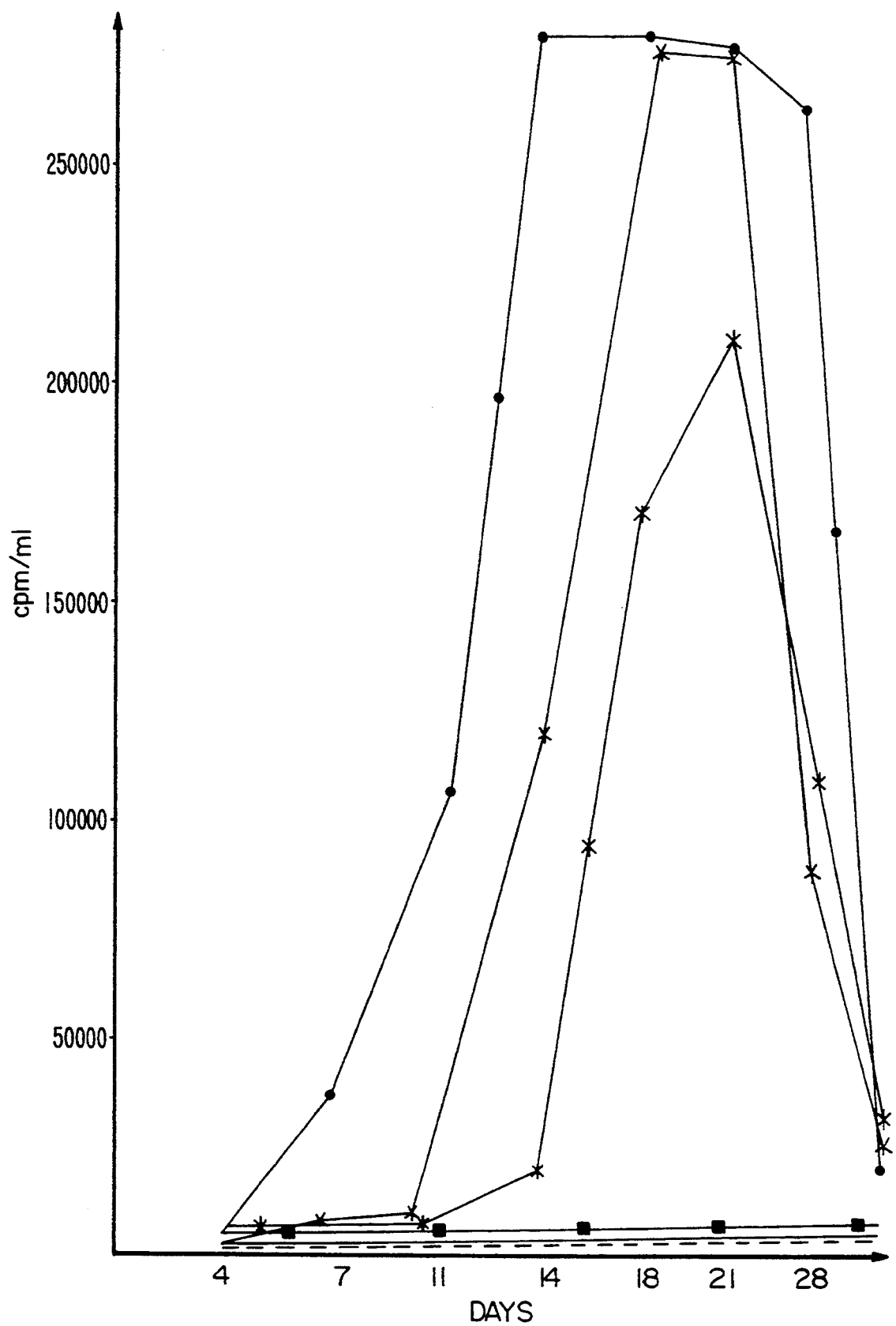
FIG. 4b shows the infective potency on activated lymphocytes of the lysates of infected or uninfected macrophages, treated or untreated, with the drug ddT.

FIG. 4b:
—✻—✻— Lysate of infected macrophages treated with $5.10^{-5}$M of ddT+lymphocytes treated with $5.10^{-5}$M of ddT.
—★—★— Lysate of infected macrophages treated with $10^{-5}$M of ddT+lymphocytes treated with $10^{-5}$M of ddT,
—●—●— Lysate of infected macrophages untreated-+untreated lymphocytes,
——— Lysate of uninfected macrophages treated with $5.10^{-5}$M of ddT+lymphocytes treated with $5.10^{-5}$M of ddT,
—■—■— Lysate of uninfected macrophages treated with $10^{-5}$ of ddT+lymphocytes treated with $10^{-5}$M of ddT,
——— Lysate of uninfected macrophages untreated+untreated lymphocytes.

Figure 4C:
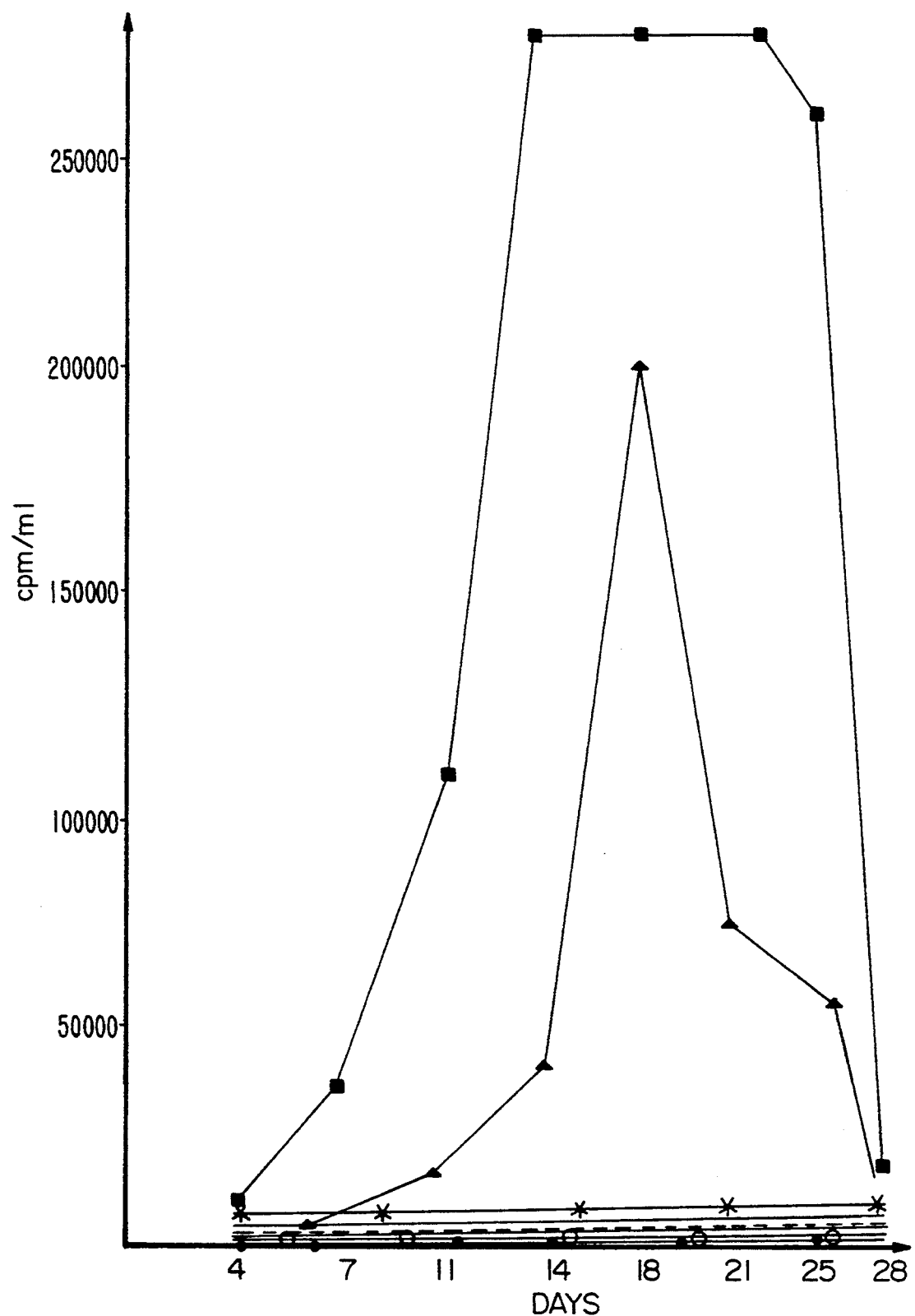
FIG. 4c shows the infective potency on activated lymphocytes of the lysates of infected or uninfected macrophages, treated or untreated, with the drug 6651.

FIG. 4c:
—●—●— Lysate of infected macrophages treated with $10^{-5}$M of 6651+lymphocytes treated with $10^{-5}$M of 6651,
—★—★— Lysate of infected macrophages treated with $10^{-6}$M of 6651+ lymphocytes treated with $10^{-6}$M of 6651,
—▲—▲— Lysate of infected macrophages treated with $10^{-7}$M of 6651+lymphocytes treated with $10^{-7}$M of 6651,
—■—■— Lysate of infected macrophages untreated-+untreated lymphocytes,
——— Lysate of uninfected macrophages treated with $10^{-5}$M of 6651+lymphocytes treated with $10^{-5}$M of 6651,
—✻—✻— Lysate of uninfected macrophages treated with $10^{-6}$M of 6651+lymphocytes treated with $10^{-6}$M of 6651,
—⊖—⊖— Lysate of uninfected macrophages treated with $10^{-7}$M of 6651+lymphocytes treated with $10^{-7}$M of 6651,
— — — Lysate of uninfected macrophages untreated-+untreated lymphocytes.

Figure 4D:
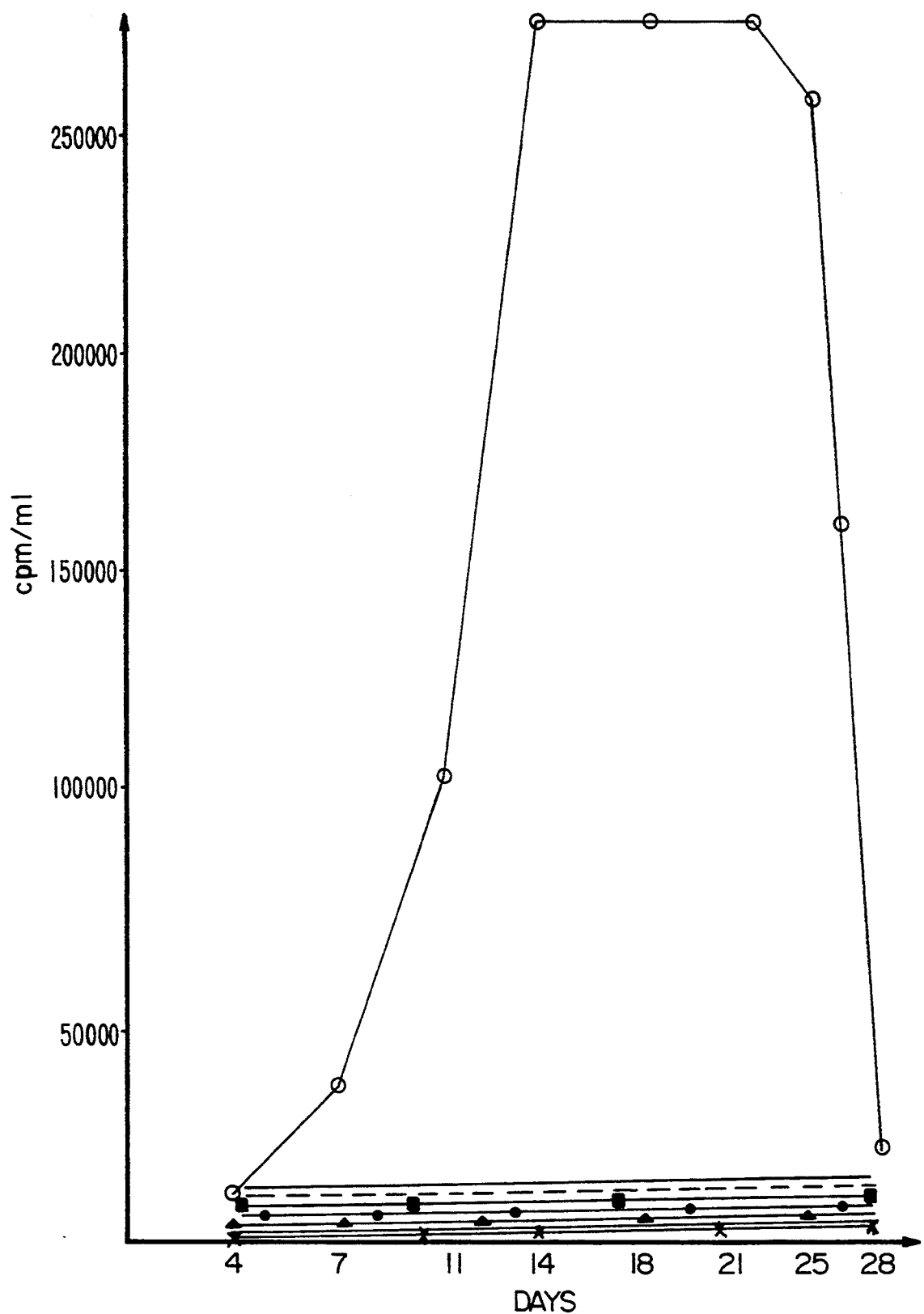
FIG. 4d shows the infective potency on activated lymphocytes of the lysates of infected or uninfected macrophages, treated or untreated, with the drug AZT.

FIG. 4d:
—★—★— Lysate of infected macrophages treated with $10^{-5}$M of AZT+lymphocytes treated with $10^{-5}$M of AZT,
—▲—▲— Lysate of infected macrophages treated with $10^{-6}$M of AZT+lymphocytes treated with $10^{-6}$M of AZT,
—■—■— Lysate of infected macrophages treated with $10^{-7}$M of AZT+lymphocytes treated with $10^{-7}$M of AZT,
—⊖—⊖— Lysate of infected macrophages untreated-+untreated lymphocytes,
— — — Lysate of uninfected macrophages treated with $10^{-5}$M of AZT+lymphocytes treated with $10^{-5}$M of AZT, —✱—✱— Lysate of uninfected macrophages treated with $10^{-6}M$ of AZT+lymphocytes treated with $10^{-6}M$ of AZT, —●—●— Lysate of uninfected macrophages treated with $10^{-7}M$ of AZT+lymphocytes treated with $10^{-7}M$ of AZT, ——— Lysate of uninfected macrophages untreated+untreated lymphocytes.

The lysates of infected macrophages treated with the drugs 6714 and ddT make it possible to obtain a vital production by activated lymphocytes. This production is comparable to the untreated lysate in the case of the drug 6714 whatever the concentration tested and for the drug ddT at a concentration of $10^{-5}M$. The viral production seems to be lower for the concentration $5.10^{-5}M$ of ddT. On the other hand, no viral production is obtained on the lymphocytes with the lysates of macrophages treated with AZT and treated with $10^{-5}M$ and $10^{-6}M$ of 6651. A low viral production is observed with the concentration of $10^{-7}M$ of the drug 6651.

Under the experimental conditions utilized, the assays carried out on the continuous cultures of macrophages show that the drugs 6651 and AZT at the concentrations $10^{-5}M$, $10^{-6}M$ and $10^{-7}M$ and the drugs.

Under the experimental conditions utilized, the assays carried out on the continuous cultures of macrophages show that the drugs 6651 and AZT at the concentrations $10^{-5}M$, $10^{-6}M$ and $10^{-7}M$ and the drugs 6714 and ddT at the concentrations $5.10^{-5}M$ and $10^{-5}M$ block the proliferation of the HIV-1 virus in the macrophages.

The experiments carried out with the lysates of macrophages show that for the drug AZT and whatever the concentration tested, $10^{-5}M$, $10^{-6}M$ and $10^{-7}M$, there is no multiplication of the HIV-1 virus at the interior of the macrophage.

In an advantageous manner, this same result is obtained with the drug 6651 at the concentrations $10^{-5}M$ and $10^{-6}M$.

On the other hand, with ddT and 6714, whatever the concentration tested, $5.10^{-6}M$ or $10^{-5}M$ and the drug 6651 at $10^{-7}M$, there is multiplication of the HIV-1 virus in the macrophages, but the escape of the virus seems to be blocked.

We claim:

1. A compound having the following formula I:

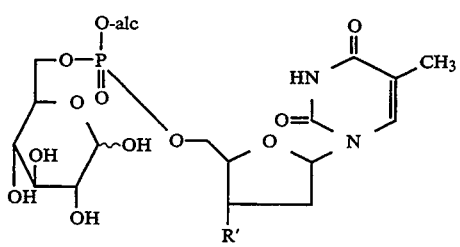

in which:
R' represents a hydrogen atom or an azido group,
alc represents a saturated or unsaturated hydrocarbon radical of 5 to 30 carbon atoms optionally substituted by an alkyl group of 1 to 4 carbon atoms, an alkoxy group of 1 to 4 carbon atoms or an amine group.

2. A glucosyl phosphotriester thymidine compound which is 6-glucosyl hexadecyl 5'-(3'-azido) thymidinyl phosphate or 6-glucosyl hexadecyl 5'-(3'-deoxy) thymidinyl phosphate.

3. A glucosyl phosphodiester thymidine compound of the following formula (II):

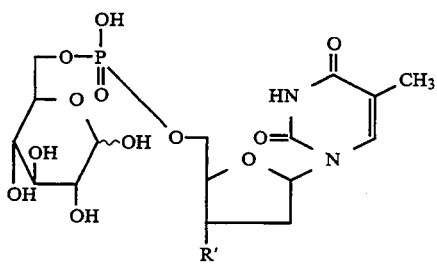

in which R' is a hydrogen or an azido group.

4. A process for the synthesis of the compounds of claim 1, comprising:
coupling (1) a glucose-6-phosphate compound of the following formula (III):

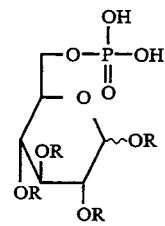

in which the radicals R, are identical or different from each other, and represent ester-linked protecting groups in the form of a salt, with (2) a thymidine compound of the following formula (IV):

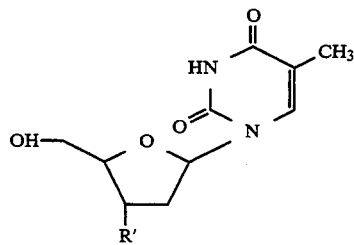

yielding the phosphodiester of the following formula (V):

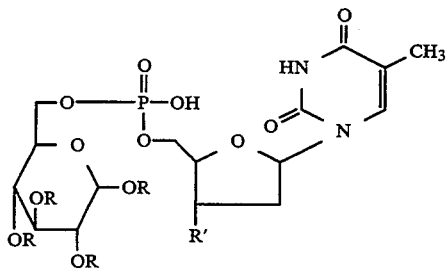

removing the protecting groups and
reacting the phosphodiester (V) with a reactive compound containing an -alc group, yielding the phosphotriester compound of the following formula (VI):

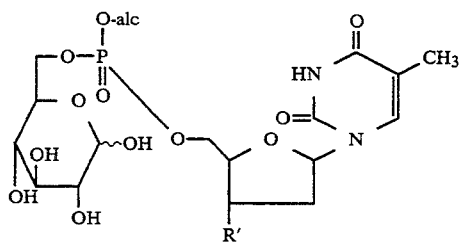

wherein R' represents a hydrogen atom or an azido group and alc represents a saturated or unsaturated hydrocarbon of 5 to 30 carbon atoms.

5. An antiviral composition comprising a compound of claim 1, in an amount effective to inhibit retroviruses, in combination with a pharmaceutically acceptable carrier.

6. An antiviral composition comprising the glucosyl phosphotriester thymidine compounds of claim 2, in an amount effective to inhibit retroviruses, in combination with a pharmaceutically acceptable carrier.

7. An antiviral composition comprising the glucosyl phosphotriester thymidine compounds of claim 3, in an amount effective to inhibit retroviruses, in combination with a pharmaceutically acceptable carrier.

8. A process for the synthesis of the compounds of claim 1, comprising:
coupling (1) a glucose-6-phosphate compound of the following formula (VII):

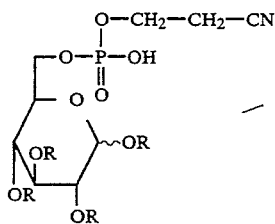

in which the radicals R, are identical or different from each other, and represent ester-linked protecting groups in the form of a salt, with (2) a thymidine compound of the following formula (IV):

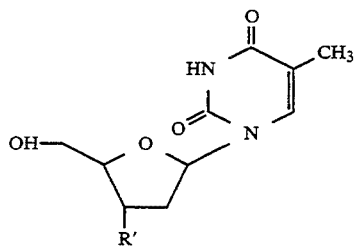

yielding the phosphodiester of the following formula (V):

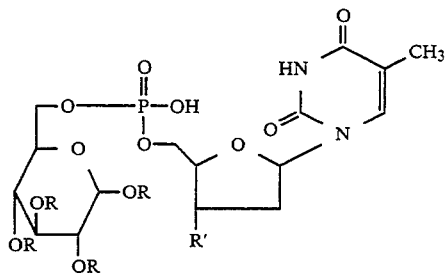

removing the protecting groups and
reacting the phosphodiester (V) with a reactive compound containing an -alc group, yielding the phosphotriester compound of the formula (VI):

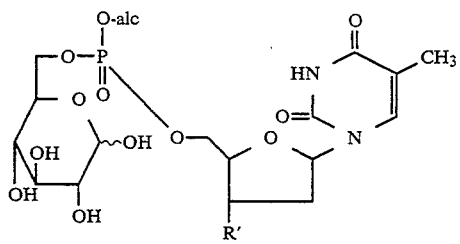

wherein R' represents a hydrogen atom or an azido group and alc represents a saturated or unsaturated hydrocarbon of 5 to 30 carbon atoms.

9. A process for the synthesis of the compounds of claim 2, comprising:
coupling (1) a glucose-6-phosphate compound of the following formula (VII):

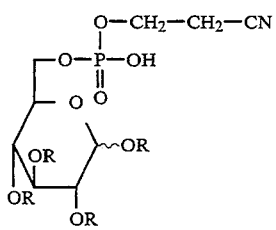

in which the radicals R, are identical or different from each other, and represent ester-linked protecting groups in the form of a salt, with (2) a thymidine compound of the following formula (IV):

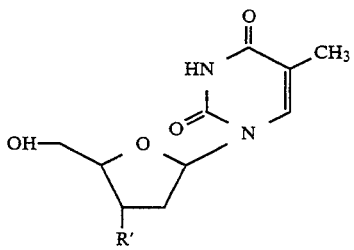

yielding the phosphodiester of the following formula (V):

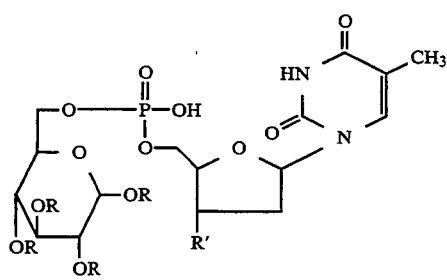

removing the protecting groups and reacting the phosphodiester (V) with a reactive compound containing an -alc group, yielding the phosphotriester compound of the following formula (VI):

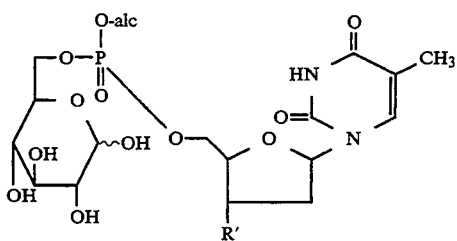

wherein R' represents a hydrogen atom or an azido group and alc represents a saturated or unsaturated hydrocarbon of 5 to 30 carbon atoms.

10. A process for the synthesis of the compounds of claim 3, comprising:

coupling (1) a glucose-6-phosphate compound of the following formula (VII):

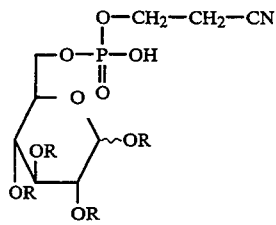

in which the radicals R, are identical or different from each other, and represent ester-linked protecting groups in the form of a salt, with (2) a thymidine compound of the following formula (IV):

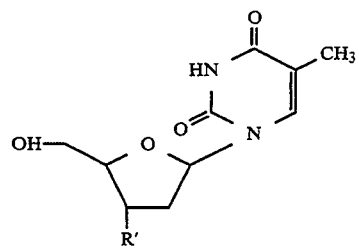

yielding the phosphodiester of the following formula (V):

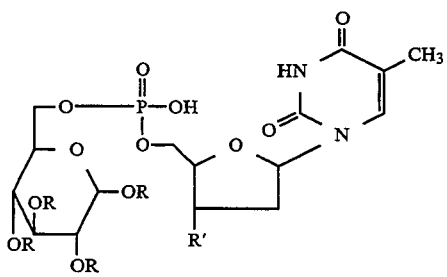

removing the protecting groups and reacting the phosphodiester (V) with a reactive compound containing an -alc group, yielding the phosphotriester compound of the following formula (VI):

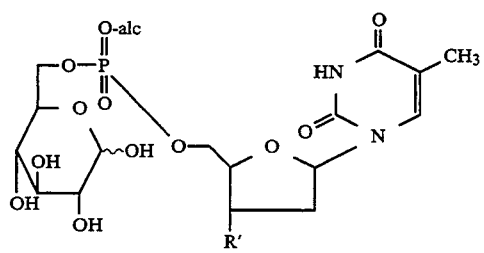

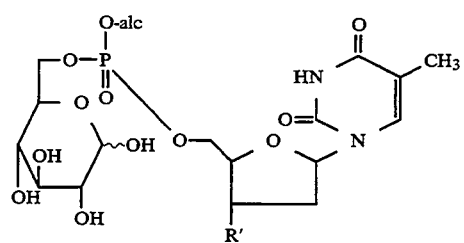

wherein R' represents a hydrogen atom or an azido group and alc represents a saturated or unsaturated hydrocarbon of 5 to 30 carbon atoms.

* * * * *